United States Patent [19]
Adiutori et al.

[11] Patent Number: 4,978,230
[45] Date of Patent: Dec. 18, 1990

[54] APPARATUS AND METHOD FOR DETERMINING HEAT TRANSFER COEFFICIENT BASED ON TESTING ACTUAL HARDWARE RATHER THAN SIMPLISTIC SCALE MODELS OF SUCH HARDWARE

[75] Inventors: Eugene F. Adiutori, Westchester; James E. Cahill, Neville, both of Ohio

[73] Assignee: General Electric Company, Cincinnati, Ohio

[21] Appl. No.: 181,128

[22] Filed: Apr. 13, 1988

[51] Int. Cl.[5] .............................................. G01N 25/00
[52] U.S. Cl. ...................................... 374/43; 374/145
[58] Field of Search ..................... 374/29, 30, 43, 44, 374/141, 144, 145, 137, 164, 179–182

[56] References Cited

U.S. PATENT DOCUMENTS

| | | | |
|---|---|---|---|
| 2,585,934 | 2/1952 | Haswell | 374/29 |
| 3,123,996 | 3/1964 | Musial | 374/43 |
| 3,509,768 | 5/1970 | Reynolds et al. | 374/115 |
| 3,592,061 | 7/1971 | Schwedland, et al. | 374/144 |
| 3,623,368 | 11/1971 | Decker | 374/144 |
| 3,672,204 | 6/1972 | Green | 374/43 |
| 4,245,500 | 1/1981 | Malang | 374/30 |
| 4,553,852 | 11/1985 | Derderian et al. | 374/30 |
| 4,595,298 | 6/1986 | Frederick | 374/144 |
| 4,644,162 | 2/1987 | Bantel et al. | 250/340 |
| 4,722,609 | 2/1988 | Epstein et al. | 374/30 |

FOREIGN PATENT DOCUMENTS 2131175  6/1984  United Kingdom ................. 374/43

Primary Examiner—Allan N. Shoap
Assistant Examiner—W. Morris Worth
Attorney, Agent, or Firm—Jerome C. Squillaro; Steven J. Rosen

[57] ABSTRACT

The heat transfer coefficient distribution on the surface of a component is measured by removing a predetermined amount of material from the surface of the component and replacing it with an insert comprising a layer of low thermal conductivity material, an array of temperature sensors, and a heater. The heat transfer coefficient is determined by applying a known amount of heat flux to the component by way of the heater and sensing the outputs of the temperature sensors. This procedure is carried out on actual hardware rather than on simplistic scale models of hardware.

40 Claims, 5 Drawing Sheets

APPARATUS AND METHOD FOR DETERMINING HEAT TRANSFER COEFFICIENT BASED ON TESTING ACTUAL HARDWARE RATHER THAN SIMPLISTIC SCALE MODELS OF SUCH HARDWARE

FIELD OF THE INVENTION

The invention of this application relates to the design of cooling systems for components used in machinery. More particularly, it relates to an apparatus and method for determining the heat transfer coefficient distribution on the surface of a cooled component. The component may be a cooled component of a gas turbine engine operated in a test environment or operated in an engine environment.

CROSS REFERENCE TO RELATED PATENT APPLICATIONS

Application Serial No. 180,919, filed Apr. 13, 1989, of Eugene F. Adiutori, entitled "APPARATUS AND METHOD FOR MEASURING THE THERMAL PERFORMANCE OF A HEATED OR COOLED COMPONENT."

Application Serial No 180,926, filed Apr. 13, 1989, of Eugene F. Adiutori, entitled "METHOD AND APPARATUS FOR MEASURING THE DISTRIBUTION OF HEAT FLUX AND HEAT TRANSFER COEFFICIENTS ON THE SURFACE OF A COOLED COMPONENT USED IN A HIGH TEMPERATURE ENVIRONMENT."

BACKGROUND OF THE INVENTION

It is well known to provide components of machinery, such as certain critical components in gas turbine engines, with cooling systems so that the machinery may be operated at higher temperatures than would be possible without such cooling systems. The higher operating temperatures permitted by such cooling systems result in increased performance and efficiency.

To design an optimum cooling system for components which will operate in a high temperature environment, it is necessary to determine the heat transfer coefficient distribution on predetermined surfaces of the cooled components. In the past, determination of the heat transfer coefficient distribution on the surface of a component was performed by extrapolating test measurements obtained from a scale model of the component.

There are, however, problems with such an approach caused by two requirements, one, that the model be affordable and, two, that it be large enough to permit the installation of instrumentation required to measure parameters which permit a determination of the heat transfer coefficient distribution. These requirements determined the degree of geometrical similarity between the model and the actual hardware and thus the closeness of the test measurement conditions to actual conditions.

Cost considerations often dictated that the geometry of the scale model was much simpler than that of the actual component. For example, gas turbine engine nozzles were usually modeled in two dimensional cascades because the cost of building and instrumenting a three dimensional cascade was prohibitive. As a result, the geometry of the model differed from that of the actual hardware.

In the case of turbine engine nozzle cascades, the geometry of the two dimensional model could not only differ, but could also differ significantly, from the actual engine geometry. In the engine geometry, the vanes in the cascade may have a twist or a variable cross section, or both. There is usually no twist or change in cross section in a model. Also in the engine geometry, the axial profile of the endwall might be contoured, whereas, in the model, the axial profile of the endwall was not contoured. The radius of the endwall in an engine is finite, whereas the endwall of the model was flat and thus had an infinite radius. The effect of these differences between the engine and the model geometries had to be accounted for by analysis if an accurate indication of engine characteristics was to be obtained from measurements on the model. The need for this analysis partially compromised the validity and accuracy of any test results In addition to simplifications resulting from the need to make the model affordable, it was often necessary to make a model which was much larger than the actual component so that the necessary measuring instruments could be installed. Models were frequently built on a scale of ten to one in each of three dimensions as compared with actual hardware, which resulted in test models which were 1000 times the volume of the actual hardware. To account for this large difference in size between the model and the hardware, the test results generally were reduced to dimensionless form. An assumption then was made that the dimensionless form accounted for the large differences in size. However, this assumption was not always valid and was seldom if ever verified.

In any event, the differences in geometry and size between the scale model and the actual component compromised the validity of heat transfer coefficient distribution test measurements obtained from the scale model. As a result, cooling systems designed with measurements obtained from a scale model often did not provide optimum cooling.

Consequently, a long felt but unfulfilled need has existed for a test which will produce accurate measurements of the heat transfer coefficient distribution on a predetermined surfaces of cooled components of machinery such as gas turbine engines.

SUMMARY OF THE INVENTION

This invention relates to an apparatus and method which satisfies the need mentioned above by permitting a measurement of the heat transfer coefficient distribution on a predetermined surface of actual hardware which is used to make a cooled component. According to one example of the invention, material is removed from a predetermined surface of the hardware in a region where it is desired to measure heat transfer coefficient distribution. The material is replaced with a low thermal conductivity material. An array of thermocouples and a heater are located next to the low thermal conductivity material and are used to make the measurements from which the heat transfer coefficient distribution may be determined.

The measurement of heat transfer coefficient may be made in an engine environment or in a test environment. The selection of whether measurement is to be made in an engine environment or in a test environment is based on the temperatures and stresses to which the hardware is exposed when it is used in an engine. For example, if the hardware is normally exposed to temperatures in excess of about 200 degrees Fahrenheit in an engine, then it is usually advisable to measure heat transfer coefficient n a test environment with this method. The heat transfer coefficient of hardware normally exposed to temperatures less than 200 degrees Fahrenheit can usually be measured in an engine environment with this method assuming that the hardware is not highly stressed in that engine environment.

BRIEF DESCRIPTION OF THE DRAWINGS

FIG. 2 is a perspective view of a portion of the nozzle cascade with part of its endwall removed for receipt of an insert in accordance with the invention of this application.

FIG. 3 is a perspective view of the entire nozzle cascade of FIG. 2 with the part of the outer endwall from which material was removed having been filled with a low thermal conductivity material.

FIG. 4 is a perspective view of a part of the nozzle cascade of FIG. 3 with fully instrumented inserts in the inner and outer endwalls FIG. 5 is a partly schematic representation of one embodiment of the invention including a cross-section of an instrumented insert.

DETAILED DESCRIPTION OF THE INVENTION

Figure 1:
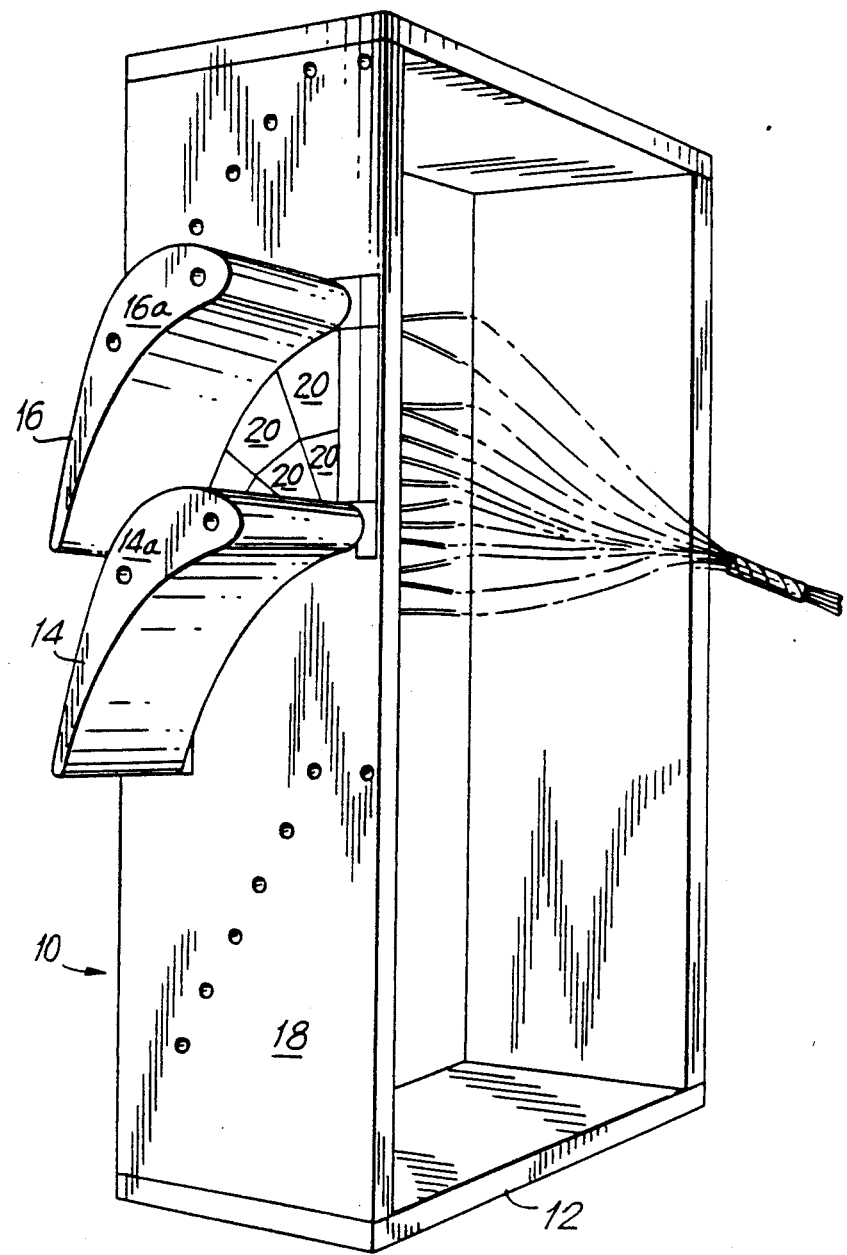
FIG. 1 shows a two dimensional model of a gas turbine engine nozzle cascade used in the past to derive the heat transfer coefficient distribution on an endwall surface of a nozzle cascade.
Figure 2:
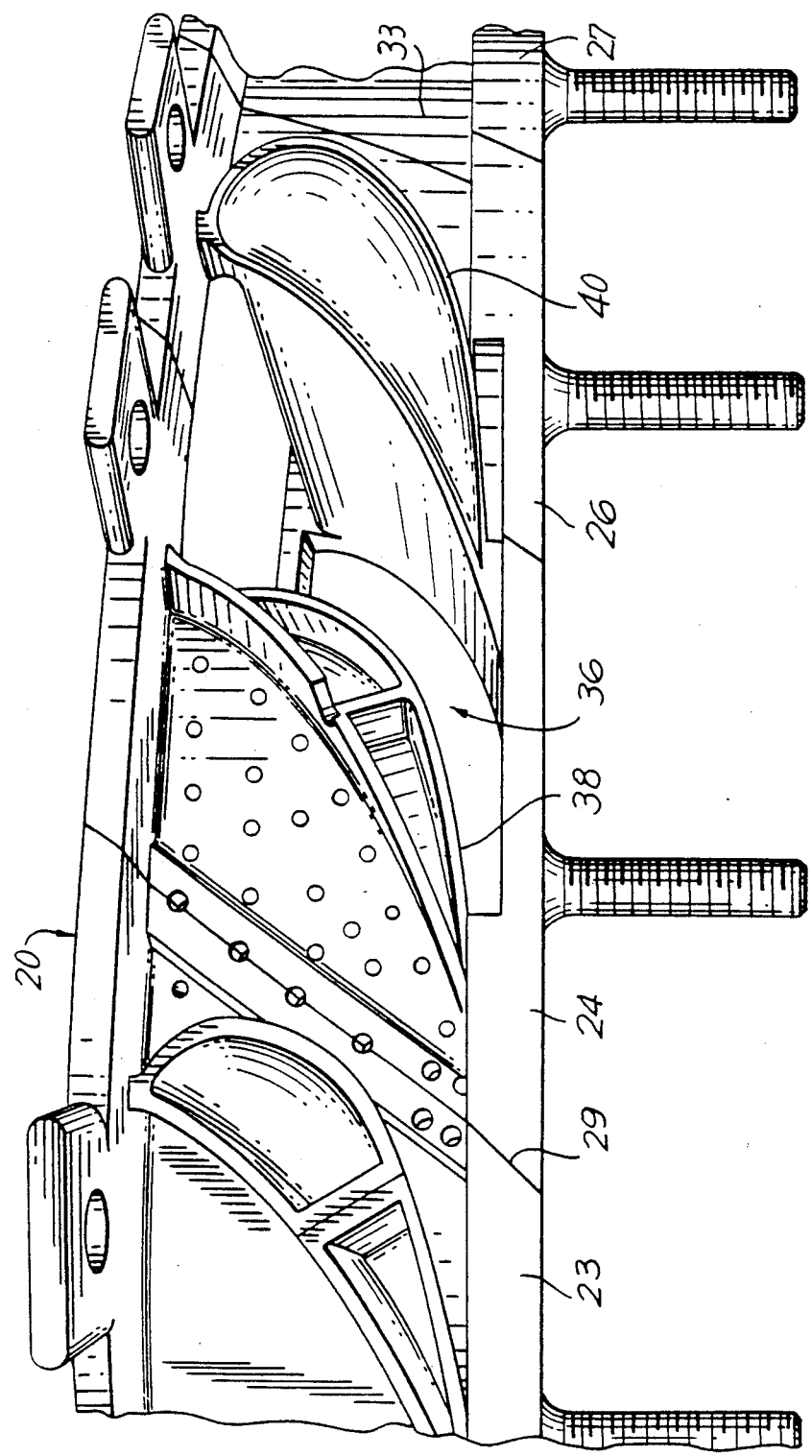
FIGS. 2-5 deal with a test structure constructed of actual engine hardware shown at various stages during its instrumentation in accordance with the invention of this application. In these Figures, the test structure is essentially an actual nozzle cascade, that is, a sector of an actual gas turbine engine nozzle.
Figure 3:
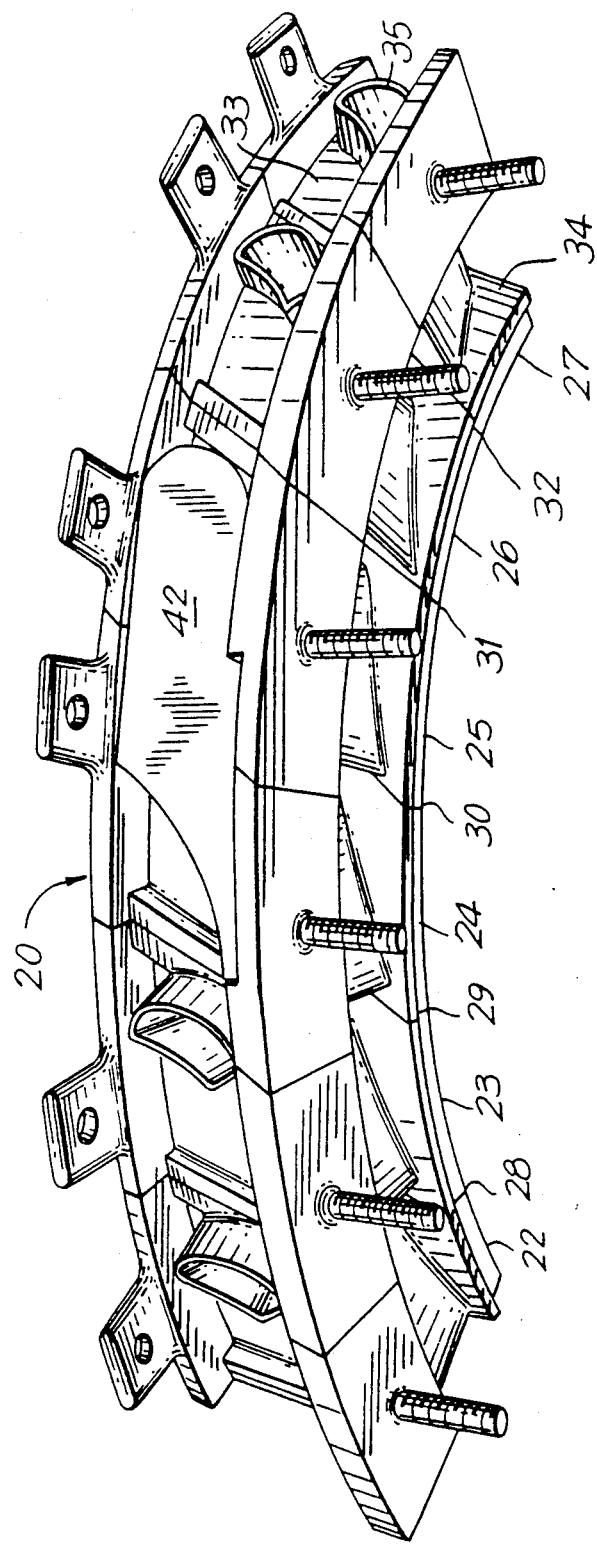

FIG. 1 shows a prior technique of measuring heat transfer coefficient distribution using a two dimensional scale model of a gas turbine engine nozzle cascade. The large scale, two-dimensional model of a nozzle cascade is generally indicated by reference numeral 10. The model 10 comprises a rectangular frame 12 supporting a pair of model airfoils 14 and 16. The model airfoils are simplified, large scale models of vanes which are situated in the flow of hot gases in a gas turbine engine. As is evident in FIG. 1, there is considerable difference between the geometry of the model and the geometry of typical engine hardware. Specifically, there is no twist in the model airfoils and the cross sections of the model airfoils are uniform. In other words, any cross section of the airfoils parallel to top surfaces 14a and 16a are identical in size, shape, and orientation. This is in contrast with the situation in actual vanes used in gas turbine engines, where there might be a twist in the vane (the cross section parallel to the surface corresponding to surfaces 14a and 16a changes in orientation as a function of radial position in the blade) or there might be a variable size or shape cross section as a function of radial position in the blade.

There are other differences between the model and the actual hardware. The geometry of surface 18, which supports the model airfoils and is intended to simulate the endwall of a nozzle cascade in a gas turbine engine, differs from the geometry of an actual endwall in a gas turbine engine. Specifically, the surface 18 is flat which means that it has an infinite radius of curvature. The actual endwall in a gas turbine engine, on the other hand, is curved around an axis passing through the center of the engine, making it generally cylindrical with a finite radius of curvature. In addition, the actual endwall may be contoured in the sense that it has a changing radius as a function of distance in a direction parallel to an axis passing through the center of the engine. This is not the case in the model of FIG. 1.

An array of thin, flat, copper inserts, some of which are indicated with reference numeral 20 in FIG. 1, is installed on surface 18 between the airfoils. Each insert is thermally insulated from its neighbors by a low thermal conductivity material around its edges. A Calrod heater and a thermocouple not shown in FIG. 1 are attached to the underside of each insert. Endwall heat transfer coefficient distribution data is obtained by applying a known amount of heat flux to surface 18, which can be accomplished by delivering known amounts of electrical power to the heaters, and measuring the temperature at each thermocouple. The heat transfer coefficient of the surface 18 in the neighborhood of each thermocouple is derived from the known amount of heat flux, the known area of the heater, the temperature measured by the thermocouples, and the mainstream temperature, as is known in the art. The results obtained for the model are then extrapolated to actual engine components by taking into account the differences in size and geometry between the model and the actual hardware. As mentioned above, this extrapolation may lead to inaccurate estimations of heat transfer coefficient distributions.

Another arrangement which has been used in the past to measure heat transfer coefficient distributions is an apparatus involving installation of foil heaters in the form of strips about one inch wide over an array of thermocouples attached to a large two dimensional plastic model. This model also differed in size and geometry from actual hardware which caused inaccurate estimations of heat transfer coefficient distributions.

These conventional methods and apparatus of measuring heat transfer coefficient distributions on scale models are sometimes inadequate because, for practical reasons, the scale models differ considerably from actual hardware. The effect of these differences must accounted for by analysis which is open to question and, therefore, partially compromises the validity and accuracy of the test results which must be extrapolated to the actual hardware geometry. The accuracy of the data obtained by this method is compromised due to the fact that the geometry and size of the scale model differ considerably from the geometry and size of the actual component.

The solution to the problems encountered in the prior methods and apparatus for measuring heat transfer coefficient distribution is to instrument actual hardware rather model hardware specially fabricated for testing. There are at least two advantages to this approach. One, the test results obtained for the dimensions and geometries of the model need not be extrapolated to the dimensions and geometries of the actual hardware. Second, in cases where the components of actual hardware are already available, it will usually be less expensive to build test structures from the available hardware components which might actually be used in a working apparatus such as an engine rather than building test structures from specially fabricated model parts.

FIGS. 2-5 show an example of the invention of this application in which a test structure composed of hardware, which actually might be used to construct a nozzle cascade used in a gas turbine engine, is outfitted with instrumented inserts for measuring endwall heat transfer coefficient distribution.

According to that example of the invention, the insert is located in an opening in the surface of the engine hardware. As described more fully below, the insert is instrumented so that the heat transfer coefficient distribution over the surface of the hardware may be determined.

Actual gas turbine engine hardware may be instrumented for measuring heat transfer coefficient distribution as follows. The procedure given here is for instrumenting a test structure in the form of a section of a nozzle constructed of parts which might be used in an actual gas turbine engine had they not been used to make the test structure.

In an actual nozzle, a pair of generally cylindrical and concentric endwalls define a generally annular passageway for the flow of fluid in the engine. Several vanes, each in the shape of an airfoil, extend radially between the endwalls to direct the flow of fluid, such as hot combustion gases, through the annular passageway. One end of each vane is attached to the inner endwall and the other end of each vane is attached to the outer end wall.

FIGS. 2-5 illustrate a test structure used to measure the heat transfer coefficient distribution of a turbine engine nozzle. In contrast to prior models used for testing, the test structure of FIGS. 2-5 is in reality a sector of an actual nozzle and not a model formed of simplistic scale model parts fabricated only for purposes of testing and not for use in an actual engine.

The sector generally indicated by reference numeral 20 comprises six smaller pieces of hardware 22-27 which are normally used to construct a nozzle in an engine. The pieces of hardware are adhered together at seams 28-32 by means of any well known technique of fastening those pieces together, such as welding. Each piece of hardware consists of a segment of what is to be an outer endwall of the cascade, a segment of what is to be an inner endwall of the cascade, and an airfoil shaped vane extending between those segments of the endwalls. See, for example, the piece of hardware labeled with reference numeral 27 in FIG. 3. The segment which is to become the outer endwall is labeled with reference numeral 33, the segment which is to become the inner endwall is labeled with reference numeral 34, and the vane is labeled with reference numeral 35. The other pieces of hardware have corresponding parts but are not labeled with reference numerals to preserve clarity in the drawings.

Instrumenting the test structure to obtain the heat transfer coefficient distribution for the endwalls is as follows. Material is first removed from the surface of the endwall where it is desired to measure heat transfer coefficient distribution, preferably to a depth of at least 0.100 inches. The removed material is replaced with a low thermal conductivity material, as more fully explained below. The entire surface of the component may be removed and replaced with low thermal conductivity material if the test structure is thin. This is the case in the apparatus of FIG. 2, where the entirety of the outer endwall has been removed in region 36 which encompasses the entire area of the endwall between vanes 38 and 40 in FIG. 2. As is clearly evident from the instrumentation shown in FIG. 4, the inner endwall between vanes 38 and 40 has also been removed.

After the material has been removed from the surface to be measured, an instrumented insert is formed in the space remaining after the removal of the material. First, the area from which material was removed is filled with a low thermal conductivity material, for example, an epoxy potting material such as Stycast. This is most clearly shown in FIG. 3 which labels the low thermal conductivity material in the space made in the outer endwall with reference numeral 42.

Passages are then formed in the low thermal conductivity material to permit routing of leads from a heater to an electrical power supply 43 which is capable of supplying a known amount of electrical power to the heater so that it delivers a known amount of heat flux to the endwall. Passages are also formed in the low thermal conductivity material to permit routing of leads from an array of thermocouples, the outputs of which are connected to circuitry which measures the signals produced by the thermocouples indicating the temperature in the vicinity of each thermocouple.

An array of thermocouples, for example, an array of wire thermocouples, is then attached to a thin metal sheet of low thermal resistance material precut to cover the region occupied by the low thermal conductivity material. One of the thermocouples is indicated by reference numeral 44 in FIG. 5; the metal sheet is indicated by reference numeral 46 in FIG. 5. The sheet may be a sheet of Nichrome about 0.003 inches thick. The thermocouples may be attached in any manner to the metal sheet so that a low thermal resistance path is established between the sheet and the thermocouple. One example of a method of attaching the thermocouples to the sheet is tack welding.

Figure 4:
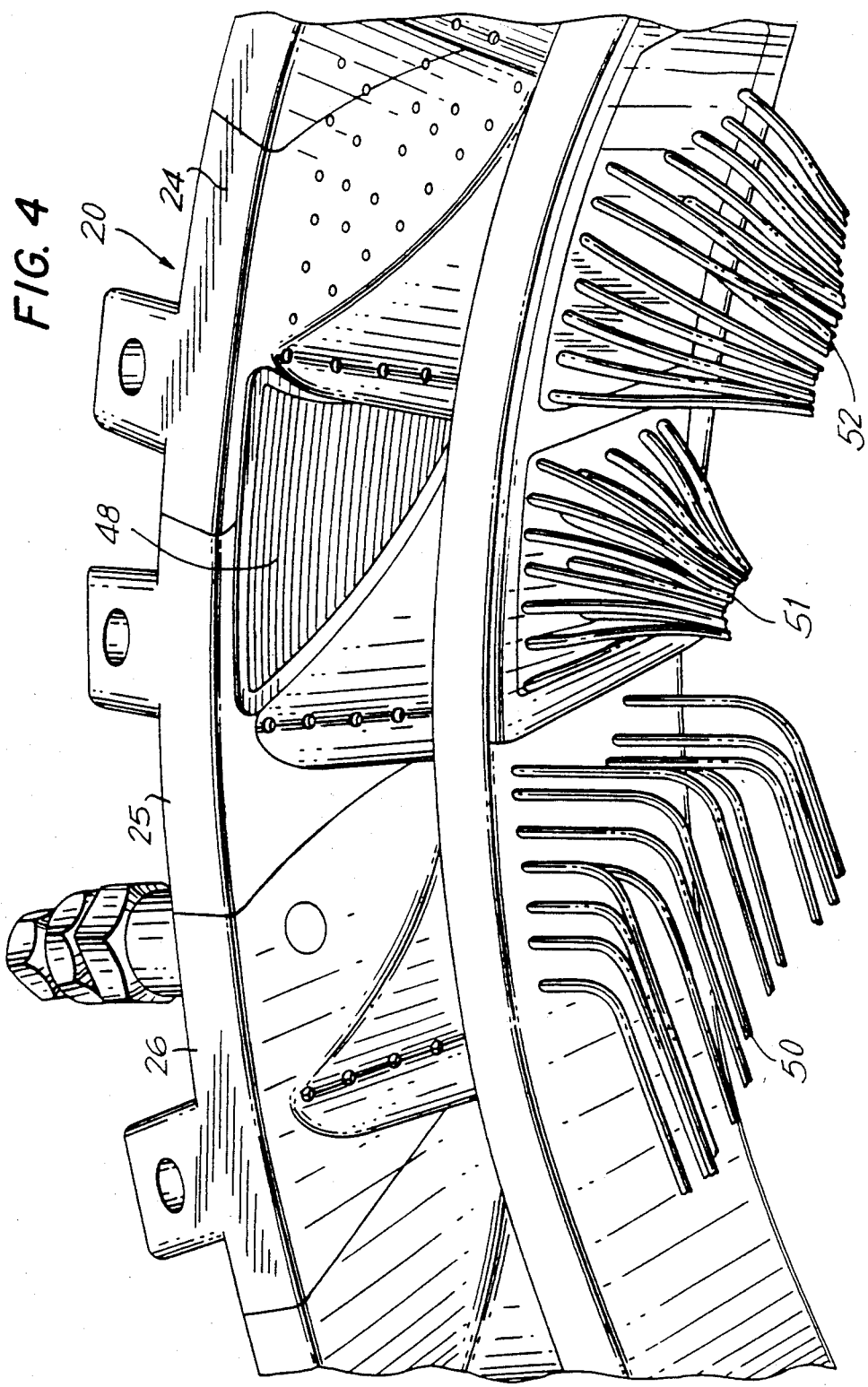
Figure 5:
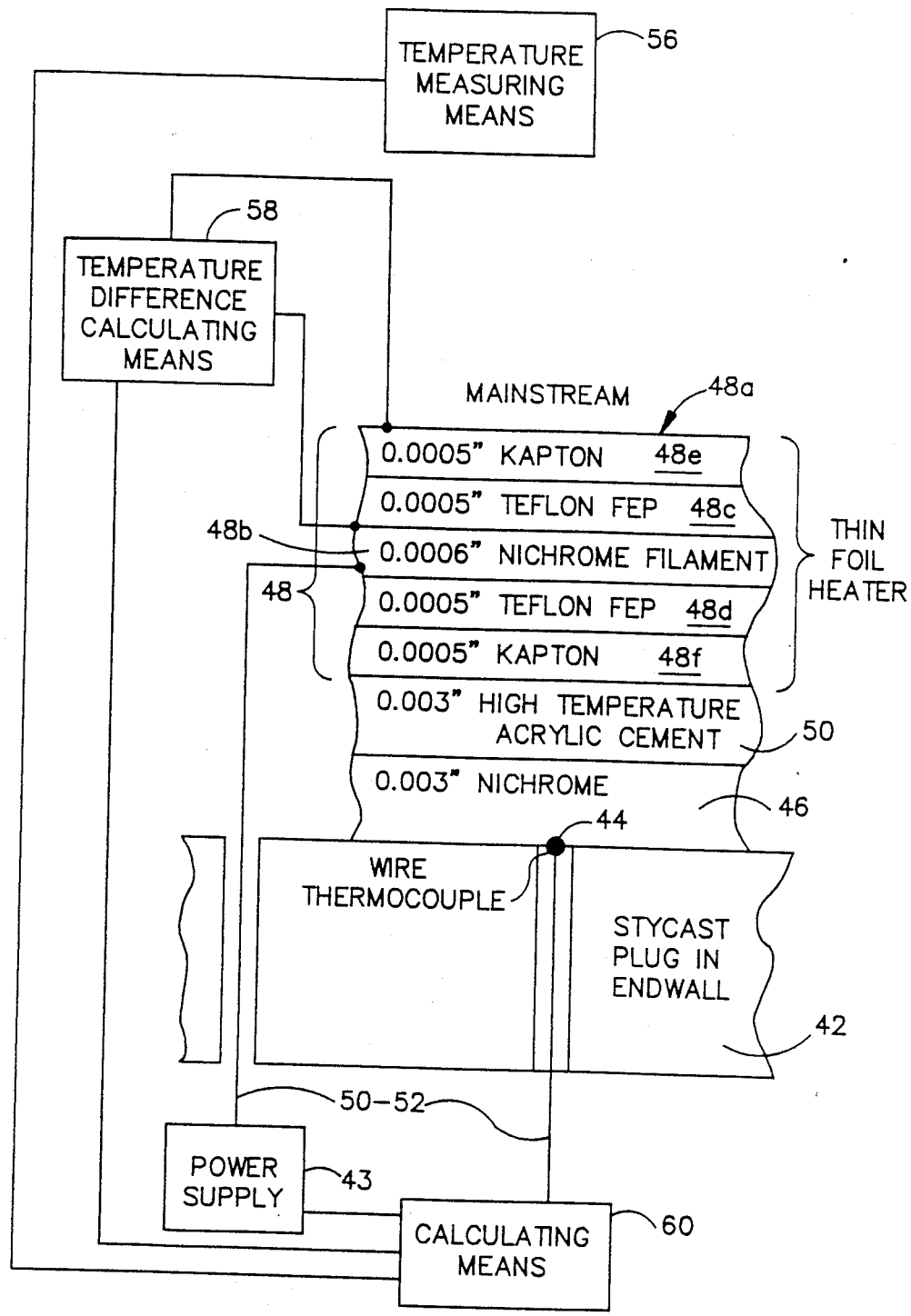

A thin foil resistive heater, one of which is indicated with reference numeral 48 in FIGS. 4 and 5, is then attached to the metal sheet, preferably with a high temperature adhesive such as a high temperature acrylic cement (layer 50 in FIG. 5) which is about 0.003 inch thick. As shown in FIG. 5, the resistance heater 48 may comprise a electrically conductive filament 48$b$ such as a Nichrome filament which may be on the order of 0.0006 inch thick, which carries electric current and produces heat when it does so. The filament 48$b$ is sandwiched between two electrically non-conductive layers. Each of the electrically non-conductive layers may comprise a layer of Teflon FEP 48$c$ and 48$d$, each of which may be about 0.0005 inch thick, and a layer of Kapton 48$e$ and 48$f$, each of which may be about 0.0005 inch thick. Such heaters may be obtained from Minco, Inc., for example, Minco Model No. HK131118742.

After the thermocouples and heater have been attached to the metal sheet, the assembly of the sheet, the thermocouples, and the heater is placed over the low thermal conductivity material and attached to that material, after the leads for the thermocouples and the heater have been routed through the passages made in the low thermal conductivity material. Next, those passages and the edges of the insert are sealed with potting compound. FIG. 4 shows sets 50-52 of wires coming from heaters and thermocouples in the inserts for the inner endwall defined by pieces of hardware 24-26. For best results, the surface of the heater showing in FIG. 4 (surface 48$a$ in FIG. 5) should be such that it approximates as closely as possible the contour of the endwall prior to removal of material for the insert.

When the endwall is heated by way of the thin foil heater, the outputs of the thermocouples permit an accurate determination of the endwall's heat transfer coefficient distribution. First a predetermined amount of heat flux is applied to the endwall. This is accomplished by way of applying a known amount of electrical power to the filaments of the heater from any generally known controllable electrical power supply 43. The heat flux is determined from the known area of the heater and the known amount of electrical power being applied to the heater.

Once the temperature of the endwall has stabilized, the outputs of the thermocouples are measured and the heat transfer coefficient may be determined from the outputs of the thermocouples and the known amount of heat flux being applied to the endwall. Specifically, the heat transfer coefficient at each thermocouple may be determined from the following equation:

$$h = Q/(T_{thermocouple} - T_{air} - \text{delta } T_{insulation}),$$

where "h" is the heat transfer coefficient, "Q" is the heat flux applied by the heater, which may be derived from the known area of the heater and the known amount of electrical power delivered to the heater, "$T_{thermocouple}$" is the temperature as measured by the thermocouple, "$T_{air}$" is the measured temperature of the air flowing past the airfoils or vane, i.e., mainstream air, as obtained by conventional temperature measuring means 56 and "delta $T_{insulation}$" is the calculated temperature difference across the material between the heater filaments and the air flowing past the airfoils or vane as obtained by conventional means 58 for calculating such temperature difference.

Delta $T_{insulation}$ may be calculated in a conventional manner using the well known equation $$Q = (kA/L) \times (\text{delta } T).$$

Which for our purposes may be restated as $$(\text{delta } T_{insulation}) = WL/kA$$

wherein k is the thermal conductivity of the insulation materials, A is the area of the heater and L is the thickness of the insulation materials in this case. The equation may be found in any standard text on conductive heat transfer such as KENT'S MECHANICAL ENGINEER' HANDBOOK, the POWER VOLUME, twelfth edition; chapter 3, pages 12 through 14 which is incorporated herein by reference. Several examples of k for various materials are given in Kent's and is normally available from the manufacturers of the materials.

Any electronic circuit or calculating means 60 such as a computer or other data processor may be provided to be responsive to the outputs of the thermocouples so that the temperature in the vicinity of each thermocouple may be measured. That electronic circuit takes signals related to the measured thermocouple temperatures and signals related to the known heat flux provided by the heater to calculate or otherwise produce electrical signals which are related to the heat transfer coefficient distribution. Of course, the heat transfer coefficient distribution may be manually computed in light of the measured temperatures and the known heat flux provided by the heater.

We claim:

1. A method for determining the heat transfer coefficient distribution on the surface of a component over which a mainstream is flowable, comprising the steps of:

removing an amount of material from the surface of the component;

replacing the removed material with an insert comprising a layer of low thermal conductivity material, an array of temperature sensors next to the layer of low thermal conductivity material, and a means for producing a predetermined amount of heat flux comprising a heater covering the array of temperature sensors which includes an electrically non-conducive layer facing toward said mainstream;

applying a predetermined amount of heat flux to the component and measuring the temperature at the location of each temperature sensor;

measuring temperature of the mainstream;

calculating the temperature difference across said electrically non-conductive layer as a function of the predetermined amount of heat flux; and deriving the heat transfer coefficient at the location of each temperature sensor from a predetermined relationship of the predetermined amount of heat flux applied to the component, the temperature measured by the temperature sensor, temperature of said mainstream and calculated temperature difference across said electrically non-conductive layer.

2. The method of claim 1, in which the removing step comprises the step of removing material from the surface of the component to a predetermined depth.

3. The method of claim 1, in which the low thermal conductivity material comprises an epoxy potting material.

4. The method of claim 1, in which the array of temperature sensors comprises an array of wire thermocouples.

5. The method of claim 1, in which the heater comprises a foil resistive heater.

6. The method of claim 1, wherein said predetermined relationship is represented by:

$$h = Q/(T_{thermocouple} - T_{air} - \text{delta } T_{insulation})$$

wherein h is the heat transfer coefficient, Q is said predetermined amount of heat flux, $T_{thermocouple}$ is said temperature at the location of said temperature sensor, $T_{air}$ is said temperature of said mainstream and delta $T_{insulation}$ is said temperature difference.

7. The method of claim 1, in which the replacing step comprises the step of replacing the removed material with an insert comprising a layer of low thermal conductivity material, an array of temperature sensors attached to a layer of low thermal resistance material, and a heater attached to the layer of low thermal resistance material.

8. A method for determining the heat transfer coefficient distribution on a predetermined surface of a turbine engine component over which a mainstream is flowable, comprising the steps of:

removing material from a predetermined surface of the component;

replacing the removed material with an insert comprising a layer of low thermal conductivity material, an array of temperature sensors next to the layer of low thermal conductivity material, and a means for producing a predetermined amount of heat flux comprising a heater covering the array of temperature sensors and the low thermal conductivity material;

applying a predetermined amount of heat flux to the component and measuring the temperature at the location of each temperature sensor;

measuring temperature of the mainstream;

calculating the temperature difference across said electrically non-conductive layer as a function of the predetermined amount of heat flux; and deriving the heat transfer coefficient at the location of each temperature sensor from a predetermined relationship of the predetermined amount of heat flux applied to the component, the temperature measured by the temperature sensor, temperature of said mainstream and calculated temperature difference across said electrically non-conductive layer.

9. The method of claim 8, in which the turbine engine component comprises at least part of a nozzle in a gas turbine engine.

10. The method of claim 9, in which the predetermined surface is at least part of the endwall of the nozzle.

11. The method of claim 8, in which the removing step comprises the step of removing material from the surface of the component to a predetermined depth.

12. The method of claim 8, in which the low thermal conductivity material comprises an epoxy potting material.

13. The method of claim 8, in which the array of temperature sensors comprises an array of wire thermocouples.

14. The method of claim 8, in which the heater comprises a foil resistive heater.

15. The method of claim 8, in which the insert further comprises a layer of low thermal resistance material between the temperature sensors and the heater.

16. The method of claim 8, in which the insert further comprises a metal layer between the temperature sensors and the heater.

17. The method of claim 15, in which the heater comprises a Nichrome filament sandwiched between two layers of electrically non-conductive material.

18. The method of claim 17, in which the two electrically non-conductive layers each comprise a layer of Kapton and a layer of Teflon FEP.

19. The method of claim 8, in which the replacing step comprises the step of replacing the removed material with an insert comprising a layer of low thermal conductivity material, an array of thermocouples attached to a layer of low thermal resistance material, and a heater attached to the layer of low thermal resistance material.

20. An apparatus for insertion into an opening in a predetermined surface of a component which is usable in a system for determining the heat transfer coefficient distribution on the predetermined surface of the component, comprising;

a layer of material having a low thermal conductivity;

an array of temperature sensors next to the low thermal conductivity layer; and a means for producing a predetermined amount of heat flux comprising a heater covering the temperature sensors and the low thermal conductivity material.

21. The apparatus of claim 20, in which the low thermal conductivity material comprises an epoxy potting material.

22. The apparatus of claim 20, in which the array of temperature sensors comprises an array of thermocouples.

23. The apparatus of claim 20, in which the heater comprises a foil resistive heater.

24. The apparatus of claim 20, further comprising a means for calculating the temperature at the location of each temperature sensor by measuring the output of each temperature sensor.

25. The apparatus of claim 24, further comprising a means for deriving the heat transfer coefficient at the location of each temperature sensor from the predetermined amount of heat flux applied to the component and the calculated temperature at the location of the temperature sensor.

26. The apparatus of claim 20, further comprising a layer of low thermal resistance material between the array of temperature sensors and the heater.

27. The apparatus of claim 20, further comprising a layer of metal between the array of temperature sensors and the heater.

28. An apparatus usable in a system for determining the heat transfer coefficient distribution on a predetermined surface of a turbine engine component, comprising:

an insert comprising a layer of low thermal conductivity material, a means for producing outputs used for calculating the heat transfer coefficient distribution on the surface of a component, said means for producing outputs comprising an array of temperature sensors next to the layer of low thermal conductivity material, and a means for producing a predetermined amount of heat flux comprising a heater covering the array of temperature sensors and the low thermal conductivity material, the insert to be located in an opening in the predetermined surface of the turbine engine component.

29. The apparatus of claim 28, in which the turbine engine component comprises at least part of a nozzle used in a gas turbine engine.

30. The apparatus of claim 29, in which the predetermined surface is at least part of the endwall of the nozzle.

31. The apparatus of claim 28, in which the opening in the predetermined surface of the component is formed by removal of material from the surface to a predetermined depth.

32. The apparatus of claim 28, in which the low thermal conductivity material comprises an epoxy potting material.

33. The apparatus of claim 28, in which the array of temperature sensors comprises an array of wire thermocouples.

34. The apparatus of claim 28, in which the heater comprises a foil resistive heater.

35. The apparatus of claim 28, further comprising a means for applying a predetermined amount of heat flux to the component and means for determining the temperature at the location of each temperature sensor.

36. The apparatus of claim 35, further comprising a means for deriving the heat transfer coefficient at the location of each temperature sensor from the predetermined amount of heat flux applied to the component and the temperature measured by the temperature sensor.

37. The apparatus of claim 28, in which the insert further comprises a low thermal resistance material between the temperature sensors and the heater.

38. The apparatus of claim 28, in which the insert further comprises a metal layer between the temperature sensors and the heater.

39. The apparatus of claim 37, in which the heater comprises a Nichrome filament sandwiched between two layers of electrically non-conductive material.

40. The apparatus of claim 39, in which the two electrically non-conductive layers each comprise a layer of Kapton and a layer of Teflon FEP.

* * * * *